United States Patent [19]

Fitch

[11] Patent Number: 5,337,364
[45] Date of Patent: Aug. 9, 1994

[54] COMMUNICATION DEVICE FOR TRANSMITTING AUDIO INFORMATION TO A USER

[75] Inventor: Frank Fitch, Vista, Calif.

[73] Assignee: Canadian Bionic Research Inc., Vancouver, Canada

[21] Appl. No.: 618,885

[22] Filed: Nov. 28, 1990

[51] Int. Cl.$^5$ .......................................... H04R 25/00
[52] U.S. Cl. .................... 381/68.3; 381/68; 340/407.1
[58] Field of Search ............... 381/68, 68.3, 151, 205, 381/200, 190, 203, 195, 197, 202, 192; 340/407.1, 407.2, 311.1

[56] References Cited

U.S. PATENT DOCUMENTS

| | | |
|---|---|---|
| Re. 23,203 | 3/1950 | Posen . |
| 2,459,325 | 1/1949 | Knowles ............... 381/68.3 |
| 2,696,527 | 12/1954 | Watson . |
| 3,629,521 | 12/1971 | Puharich et al. ............... 179/107 R |
| 3,766,331 | 10/1973 | Zink ............... 179/107 R |
| 3,787,641 | 1/1974 | Santori ............... 381/151 |
| 3,875,932 | 4/1975 | Wachspress ............... 128/24 R |
| 4,139,742 | 2/1979 | Walker ............... 381/68 |
| 4,380,689 | 4/1983 | Giannetti ............... 381/68 |
| 4,395,601 | 7/1983 | Kopke et al. . |
| 4,472,605 | 9/1984 | Klein ............... 381/195 |
| 4,581,491 | 4/1986 | Boothroyd ............... 381/68 |
| 4,612,915 | 9/1986 | Hough et al. ............... 381/68.3 |
| 4,728,934 | 3/1988 | Pfander et al. ............... 381/68 |

FOREIGN PATENT DOCUMENTS

| | | |
|---|---|---|
| 0088154 | 8/1982 | European Pat. Off. . |
| 0863082 | 1/1953 | Fed. Rep. of Germany ...... 381/200 |
| 1180456 | 6/1959 | France ............... 381/195 |
| 2577739 | 8/1986 | France ............... H04R 25/00 |
| 0628916 | 10/1978 | U.S.S.R. ............... 381/68.3 |
| 0705100 | 3/1954 | United Kingdom ............... 381/195 |

OTHER PUBLICATIONS

Feinwerktechnik & Messtechnik, vol. 98, No. 7/8, Aug. 15, 1990, DE pp. 291-293; Blume: 'Besser hören mil elktromagnetischen Wandlersystemen'.

Primary Examiner—Curtis Kuntz
Assistant Examiner—Huyen D. Le
Attorney, Agent, or Firm—Fitzpatrick, Cella, Harper & Scinto

[57] ABSTRACT

A communication device for transmitting audio information includes a compact casing which houses processing circuitry. The processing circuitry converts input audio signals into transducer driving signals. A miniaturized microphone is mounted in the casing for receiving the input audio signals. The input audio signals are then amplified and filtered to appropriate signal levels by the processing circuitry. Once the input audio signals have been processed in this manner they are applied to a driver which outputs transducer driving signals analogous to the input audio signals. The transducer driving signals are received by a transducer assembly worn by a user and energize a pair of coils located on opposite sides of an armature forming part of the transducer assembly. The electromagnetic forces generated by the coils when energized cause the armature to move. Movement of the armature in turn drives a plunger so that the plunger moves in a vibrational pattern analogous to the input audio signals. The plunger contacts the skin of the user so that the vibrational pattern is received by cutaneous nerve receptors on the user's body or by the user's ears via bone conduction. This vibrational information is then transmitted to the user's brain for processing. A pair of springs are located on opposite sides of the armature and bias the armature and plunger so that they move to a datum in the absence of driving signals. The spring also oppose movement of the armature and plunger when driven by the coils.

41 Claims, 8 Drawing Sheets

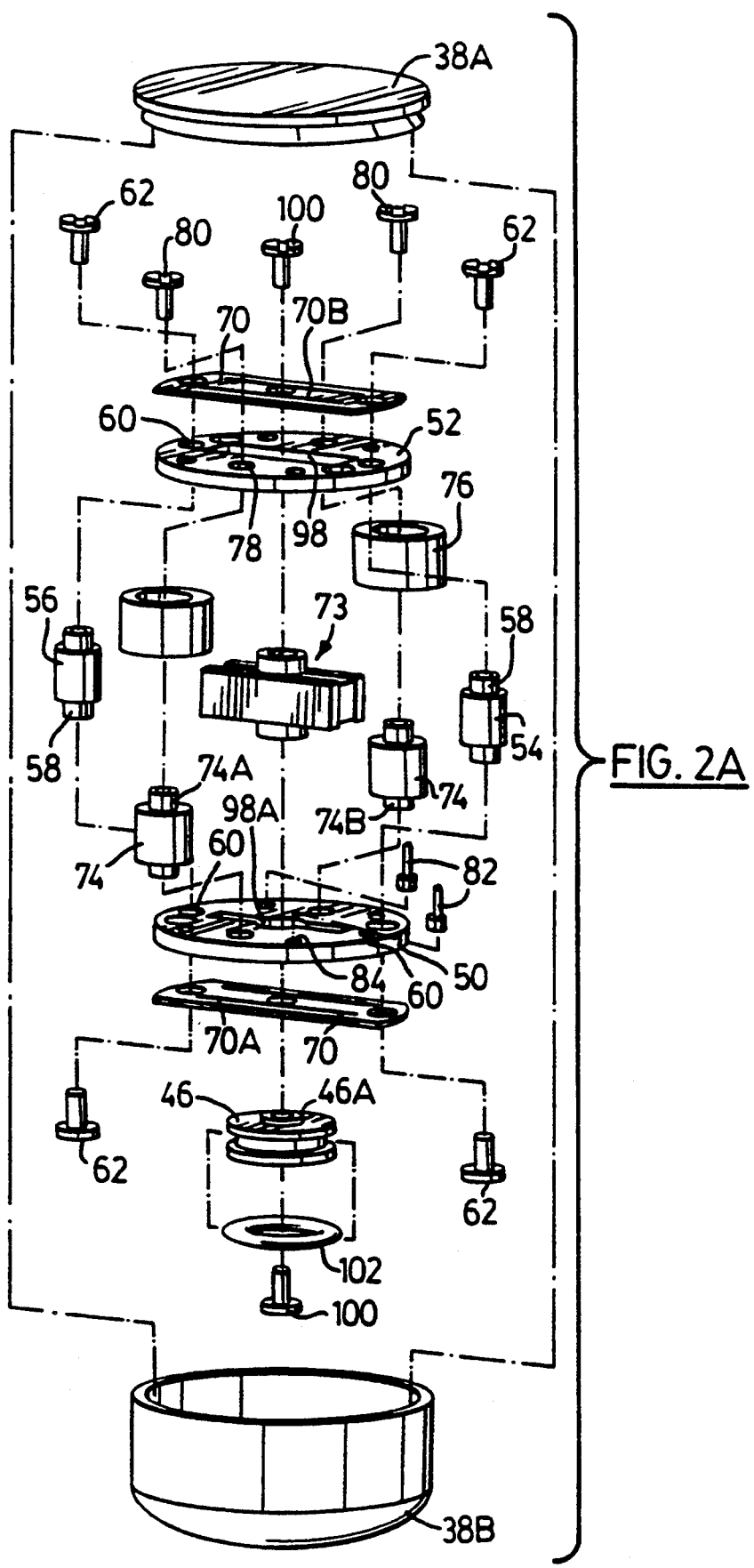

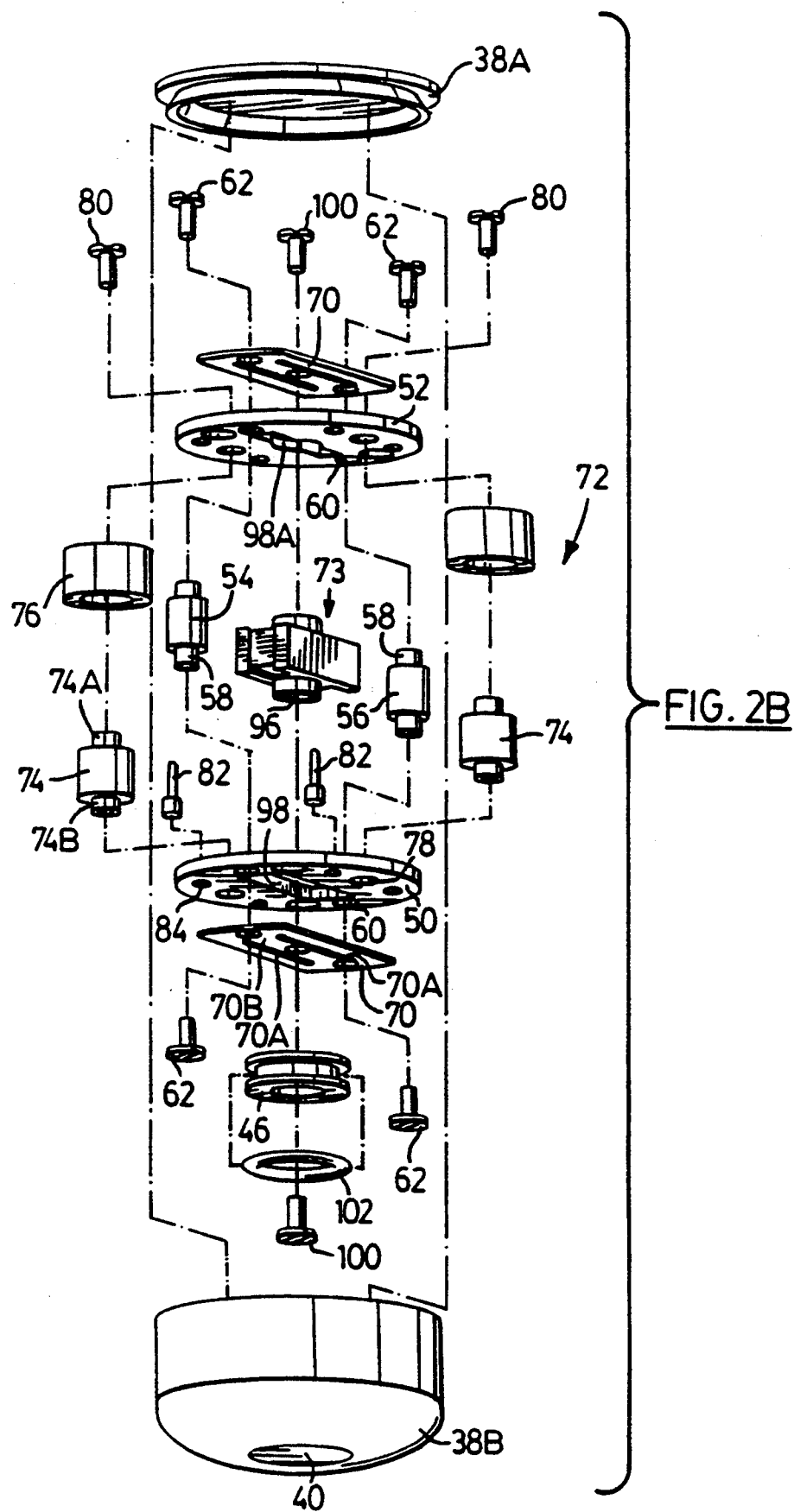

COMMUNICATION DEVICE FOR TRANSMITTING AUDIO INFORMATION TO A USER

FIELD OF THE INVENTION

The present invention relates to a device for transmitting signals such as voice signals to a user and in particular to a device which transmits audio signals to cutaneous nerve receptors or to the bone in such a way that the receptors or ears transmit intelligible signals to the brain.

BACKGROUND OF THE INVENTION

Until relatively recently it has been generally thought that a person was capable of hearing audio frequency vibrations only with the ears and that it was necessary to utilize the ear structure for effective communication. It has also been known that the body has cutaneous nerve receptors which sense mechanical vibrations in the air and transmit those vibrations to the brain, bypassing the ear structure.

In the medical profession, it has been found that many people who are partially deaf are afflicted with sound distortion, so that even though they hear particular sounds or words, the sounds or words become so distorted by the inner ear, they are indecipherable. Accordingly, if such a deaf person can be trained to bypass the inner ear in order to "hear", this distortion may be eliminated.

A cutaneous communication device for transmitting audio information to the cutaneous nerve receptors located at the wrist of a user to allow the user to by-pass the ear structure and "hear" the audio information is described in U.S. Pat. No. 4,139,742 to Walker which has been assigned to the assignee of the present application. This device includes a conventional microphone connected by a cable and jack to an audio frequency amplifier. The amplifier provides signals to a mechanical transducer assembly mounted on a band to be worn around the wrist of a user. The transducer assembly includes a plunger which projects outwardly of the transducer assembly housing to contact the skin. The plunger moves towards and away from the skin when signals are applied to the transducer via the amplifier in response to input audio signals received by the microphone.

The transducer assembly operates to move the plunger in a vibrational pattern analogous to the audio signals received by the microphone. The cutaneous nerve receptors at the wrist of the user discriminate between the vibrations caused by the plunger and extraneous noise to allow the brain to interpret the audio signals received by the microphone. This permits audio communication to occur without use of the inner ear. Although the operation of this device is satisfactory, it is always desirable to enhance performance and reduce complexity and size.

In addition to assisting the hearing impaired, there are many other situations in which it is difficult or undesirable to communicate verbally by transmitting messages through the air. For example, it is extremely difficult to communicate audibly in industrial plants where ear muffs are worn. Also, motorcycle riders and their passengers have difficulty talking to one another because of noise generated by both the motorcycle engine and the wind. Furthermore, there may be situations in which a person needs to receive both audio communication and cutaneous nerve communication. For example, spoken messages can be received by radio receiver and transmitted cutaneously to the brain while the person is otherwise occupied or otherwise communicating verbally. Such a device could have use in a "bell boy" call director type of communication system. Moreover, when conducting surveillance it is often undesirable to communicate verbally with other parties although communication between the parties is desirable.

Accordingly, it is an object of the present invention to provide a novel communication device for transmitting audio information to a user and a transducer for use therein.

SUMMARY OF THE INVENTION

Broadly stated the present invention provides a communication device for transmitting audio information to a user comprising:
input means for receiving input audio signals;
processing means in communication with said input means and converting said input audio signals into transducer driving signals;
a transducer assembly to be worn by a user and being in communication with said processing means, said transducer assembly including a plunger member moveable to contact said user; drive means responsive to said driving signals and moving said plunger member to contact said user in a vibrational pattern analogous to said input audio signals; and biasing means located on opposite sides of said drive means for opposing movement of said plunger member and for returning said plunger member to a datum in the absence of said driving signals.

In another aspect of the present invention there is provided a transducer assembly for use in a communication device for transmitting audio information to a user comprising:
a casing;
a plunger member within said casing and being moveable through an aperture in said casing to contact said user;
drive means within said casing and being responsive to driving signals analogous to audio information to be transmitted to said user to move said plunger member to contact said user in a vibrational pattern according to said driving signals; and
biasing means located opposite sides of said drive means for opposing movement of said plunger member and for returning said plunger member to a datum in the absence of said driving signals.

In still yet another aspect of the present invention there is provided a transducer assembly for use in a communication device for transmitting audio information to a user comprising:
a casing;
a plunger member within said casing and being moveable through an aperture in said casing to contact said user;
a driving member within said casing and being operable to move said plunger member to contact said user;
at least two drive means responsive to driving signals analogous to audio information, said drive means being located on opposite sides of said driving member and actuating said driving member thereby to move said plunger member so that said plunger member contacts said user in a vibrational pattern according to said driving signals; and biasing means for returning said plunger member to a datum in the absence of said driving signals.

Preferably, the drive means includes an armature moveable in response to the driving signals which in turn moves the plunger member. It is also preferred that the biasing means is constituted by a pair of springs located on opposite sides of the armature.

Preferably, the drive means also includes a pair of coils with each coil surrounding a steel core and being located on opposite sides of the armature, the coils generating an electromagnetic force when energized by the driving signals which cause the armature to move the plunger member.

It is also preferred that the armature includes a core member formed from stainless steel. Magnets are fastened to one set of opposed sides of the core member while pole pieces formed from cold rolled steel are secured to the other set of opposed sides of the core member. The pole pieces also contact the magnets so that the armature in effect functions as a larger continuous magnet. Preferably, the magnets are formed from Samarium Cobalt and that the pole pieces and magnets are secured to the core member and to each other via cyanoacrylate.

It is also preferred that the audio input means is in the form of a miniaturized microphone and that the processing means and microphone are located all within a single compact housing.

In one embodiment, it is preferred that the transducer assembly is worn by the user adjacent a portion of the user's body having cutaneous nerve receptors. This allows the cutaneous nerve receptors to convey the vibrational pattern received via the plunger member to the user's brain for processing.

In another embodiment, it is preferred that the transducer assembly is mounted in an article worn on the user's head so that the vibrational pattern imparted to the user by the plunger member is conveyed to the user's ears via bone conduction.

In the first embodiment, it is preferred that the transducer assembly is secured to a band similar to a wrist watch band to allow the assembly to be secured to the user's wrist. In the second embodiment it is preferred that the transducer assembly is mounted in a safety helmet or in the frame work of a pair of glasses to be worn by the user.

The present invention provides advantages in that due to the transducer assembly construction, the size of the device is reduced significantly as compared with prior art devices. Moreover, the provision of the biasing means in the form of a pair of springs provide a preset load on the armature to ensure that the armature and plunger member move to a datum when the transducer assembly is not energized by driving signals and oppose movement of the armature and hence the plunger member, during response to driving signals. In addition, due to the use of a miniaturized microphone and enhanced amplification and driving circuitry, all of the device components except for the transducer assembly are packaged in a compact housing designed to facilitate use and portability.

BRIEF DESCRIPTION OF THE DRAWINGS

Embodiments of the present invention will now be described by way of example only with reference to the occupying drawings in which:

FIG. 2a is an exploded perspective view taken from the side and from above of a portion of the device shown in FIG. 1;

FIG. 2b is an exploded perspective view taken from the side and from below of the portion shown in FIG. 2a;

FIG. 4b is an end view of the element shown in FIG. 4a;

FIG. 4c is a side view of the element shown in FIG. 4a;

DETAILED DESCRIPTION OF THE PREFERRED EMBODIMENTS

The present invention provides a communication device for transmitting audio information to a user without transmitting the information through the air which is useful in a number of different environments. In the medical environment, the present device can be used to assist the hearing impaired. In noisy environments, the device can be used to facilitate communications between parties. In the communications industry, the present device permits information to be transferred to a party who may be engaged in other verbal communications. In the surveillance environment, the present device can be used to allow communications to take place between parties without creating excessive audible sound which may alarm the subject being watched. The present device is also useful in the telecommunications industry for use in conjunction with a telephone or other similar device.

Figure 1:
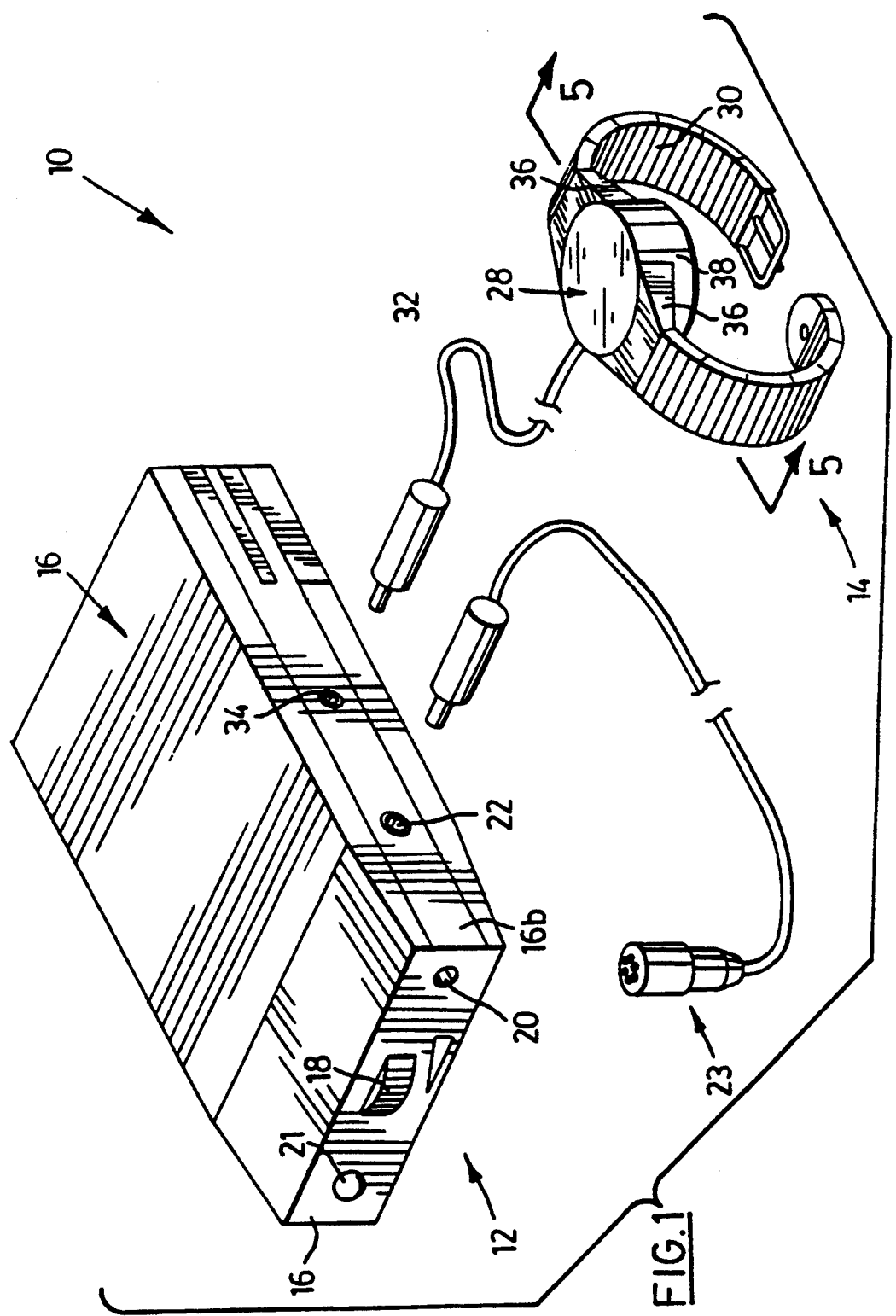
FIG. 1 is a perspective view of a cutaneous communication device for transmitting audio information to a user.
Figure 3:
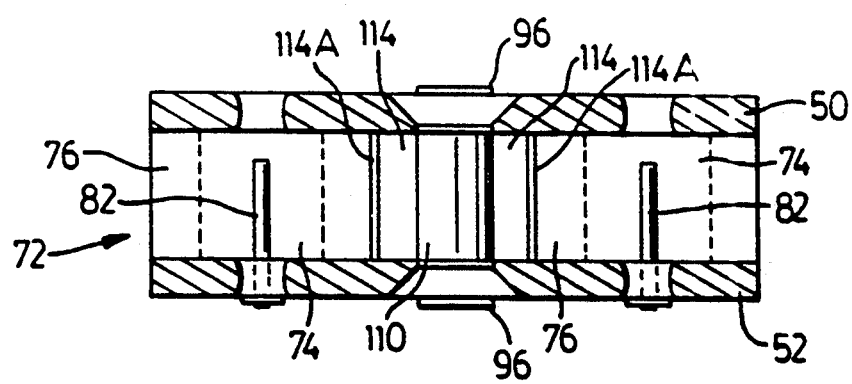
FIG. 3 is a side view of some assembled elements forming part of the portion shown in FIGS. 2a and 2b.

Referring now to FIG. 1, a first embodiment of a communication device for transmitting audio information to a user is shown and is generally indicated by reference numeral 10. The device 10 is particularly suitable for transmitting audio information to the cutaneous nerve receptors located at a user's wrist as will be described. The device 10 comprises mainly two sections, namely an audio signal processing section 12 and a transducer assembly 14.

The processing section 12 includes a housing 16 in which processing circuitry (best seen in FIGS. 6 and 7) is located. A volume adjust 18 in the form of a rotatable dial extends through one wall 16a of the housing 16. A miniaturized microphone 20, preferably of the type manufactured by Knowles Electronics Inc. Illinois, U.S.A. is located within the housing adjacent an aperture formed in the wall 16a of the housing. The volume dial 18 permits the signal level of audio signals received by the microphone 20 to be raised or lowered as desired and allows the device 10 to be shut off. A low battery indicator in the form of an LED 21 extends through the wall 16a as well. An input audio signal jack 22 is provided on another wall 16b of the housing and allows the microphone 20 to be by-passed so that another input audio signal source can be used such as an external microphone as shown and indicated by reference numeral 23. A power supply Jack (not shown) is provided on one of the other walls of the housing 16 and allows a power source forming part of the processing circuitry to be recharged or by-passed if desired.

The housing 16 is of a compact design to facilitate carrying by a user in a convenient location without inhibiting the microphone's reception of input audio signals.

Figure 5:
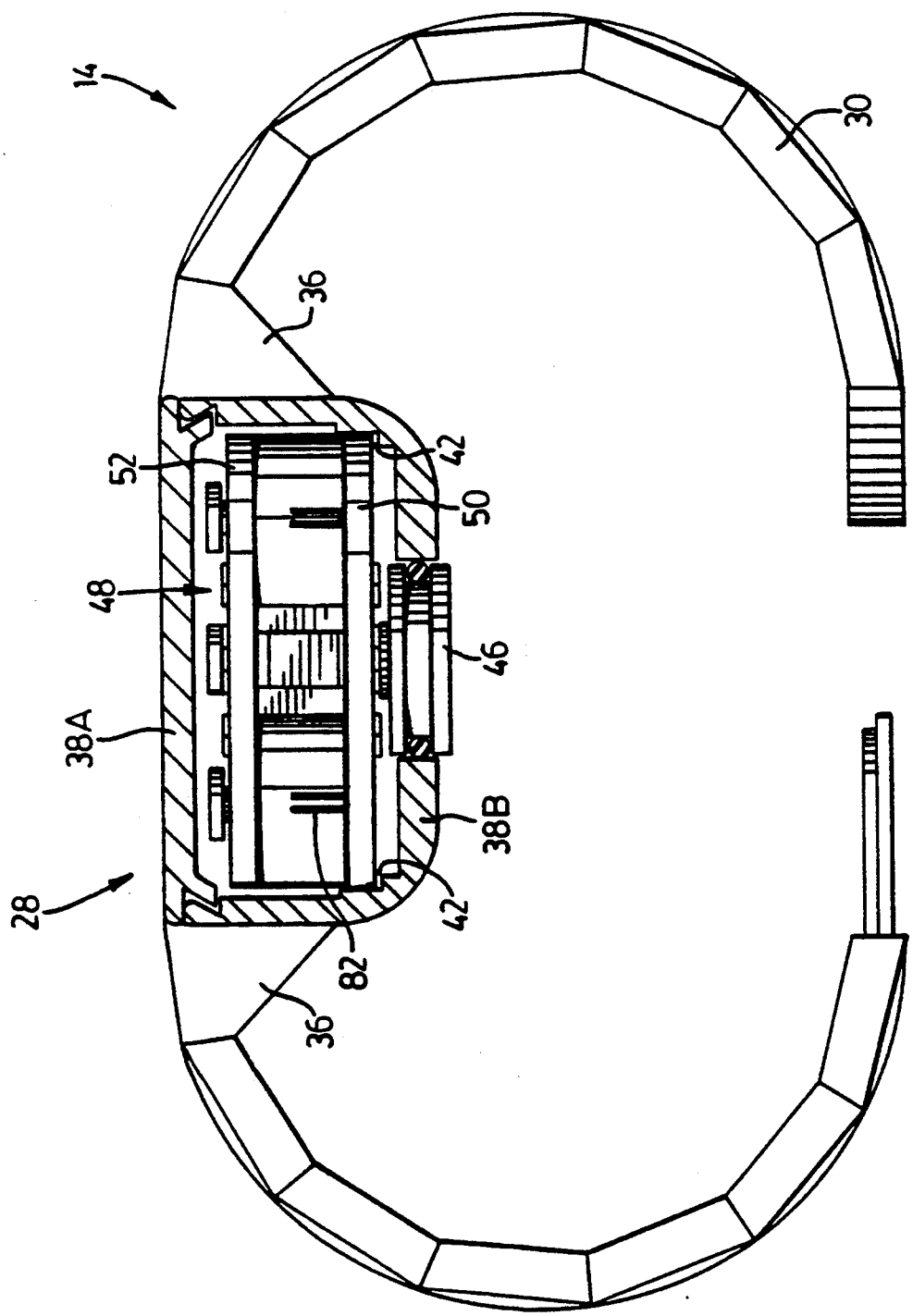
FIG. 5 is a section of FIG. 1 taken along line 5—5.

Looking at the transducer assembly 14 as best shown in FIGS. 1 and 5, it can be seen that the transducer assembly 14 includes a transducer 28 mounted on a band 30 which can be conveniently secured around the wrist of a user. An electrical cable 32 extends from the transducer 28 and is removeably received in a transducer jack 34, also provided on the housing wall 16b. The transducer 28 includes a metal wrist watch housing 36 which receives a plastic transducer casing 38 formed from Delrin. The casing 38 includes an upper section 38a having a generally flat, upper surface and a lower dome-shaped section 38b with the upper and lower sections snap fitting together.

Disposed within the transducer casing 38 is a plunger 46 which passes through an aperture 40 formed in the lower section 38b to contact the skin of the user when actuated by a drive mechanism 48. The excursion of the plunger 46 from its rest position when driven by the drive mechanism is typically ±0.015 inches although preferably the maximum excursion of the plunger 46 is limited to ±0.01 inches from its rest position. As can been seen, the bottom section 38b of the casing 38 has an annular ridge 42 formed along its inner wall upon which the drive mechanism 48 is secured.

FIGS. 2a and 2b best illustrate the drive mechanism 48 and as can be seen it includes a matched pair of generally circular, solenoid frame members 50, 52 formed from cold rolled steel. The frame members 50,52 have a plurality of circular bores along with a rectangular passage formed therethrough. The two frame members are spaced apart along a longitudinal axis X and are positioned by a pair of generally cylindrical, diametrically located spacers 54 and 56 so that the bores and passage in each of the frame members remain aligned.

Each spacer 54,56 includes a portion of reduced diameter 58 at its opposed ends which seat in bores 60, formed through the frame members. The frame members 50, 52 are secured to the spacers 54, 56 by steel screws 62, which also pass through the bores 60, and threadably engage with internal threads provided in the spacers 54,56. The screws 62 also act to retain a beryllium-copper spring 70, against the outwardly facing side of each frame member. A pair of parallel slots 70a are formed in each spring 70 to define a band 70b having increased flexibility. Each band 70b is positioned to overlie the rectangular passage formed in its associated frame member in a rest position and is dimensioned so that it can move into the passage when flexed.

A pair of coil assemblies 72 and an armature assembly 73 are also positioned between the two spaced frame members. As can be seen, the coil assemblies 72 are diametrically located with respect to the longitudinal axis X. Each coil assembly includes a coil core 74 formed from cold rolled steel and a coil 76 surrounding the core 74 having approximately 350 turns. Each coil core 74 also includes an upper portion 74a of reduced diameter at one end thereof and a lower portion 74b of reduced diameter at the other end thereof with the portions being received in bores 78 provided through the frame members. The coil cores 74 are provided with internal threads at their upper end which receive screws 80 passing through frame member 50 to secure the coil assemblies 72 to the frame member 50. The screws 80 do not contact the springs 70 and remain flush against the outwardly facing side of the frame member 50. The other end 74b of each coil core 74 is end punched into the frame member 52 to provide a secure mounting. The coil 76 of each coil assembly 72 is electrically connected to a pair of electrical leads 82 passing through bores 84 extending through the frame member 52.

Figure 4B:
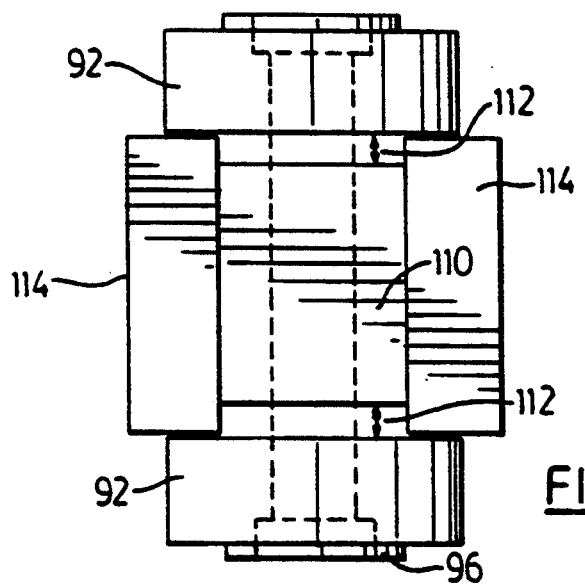
Figure 4C:
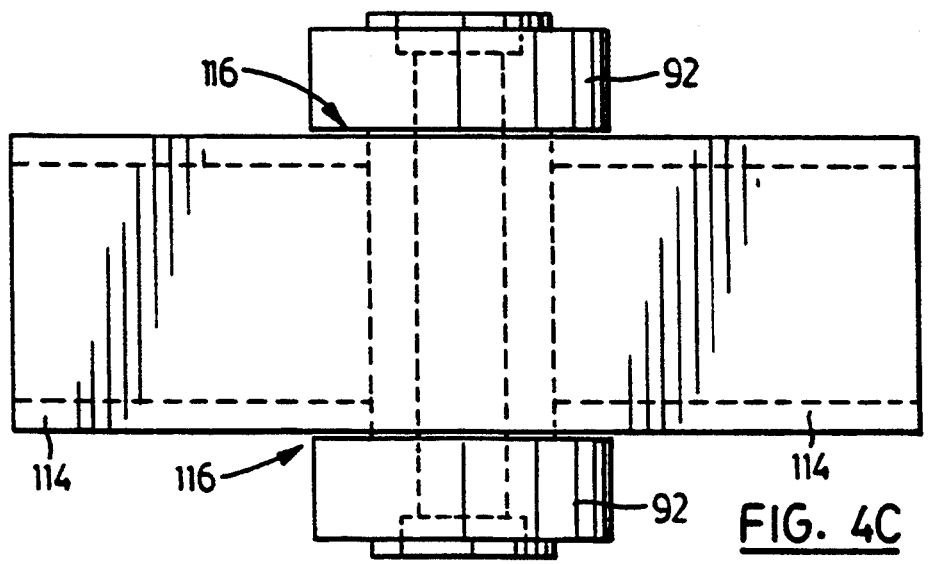
Figure 4A:
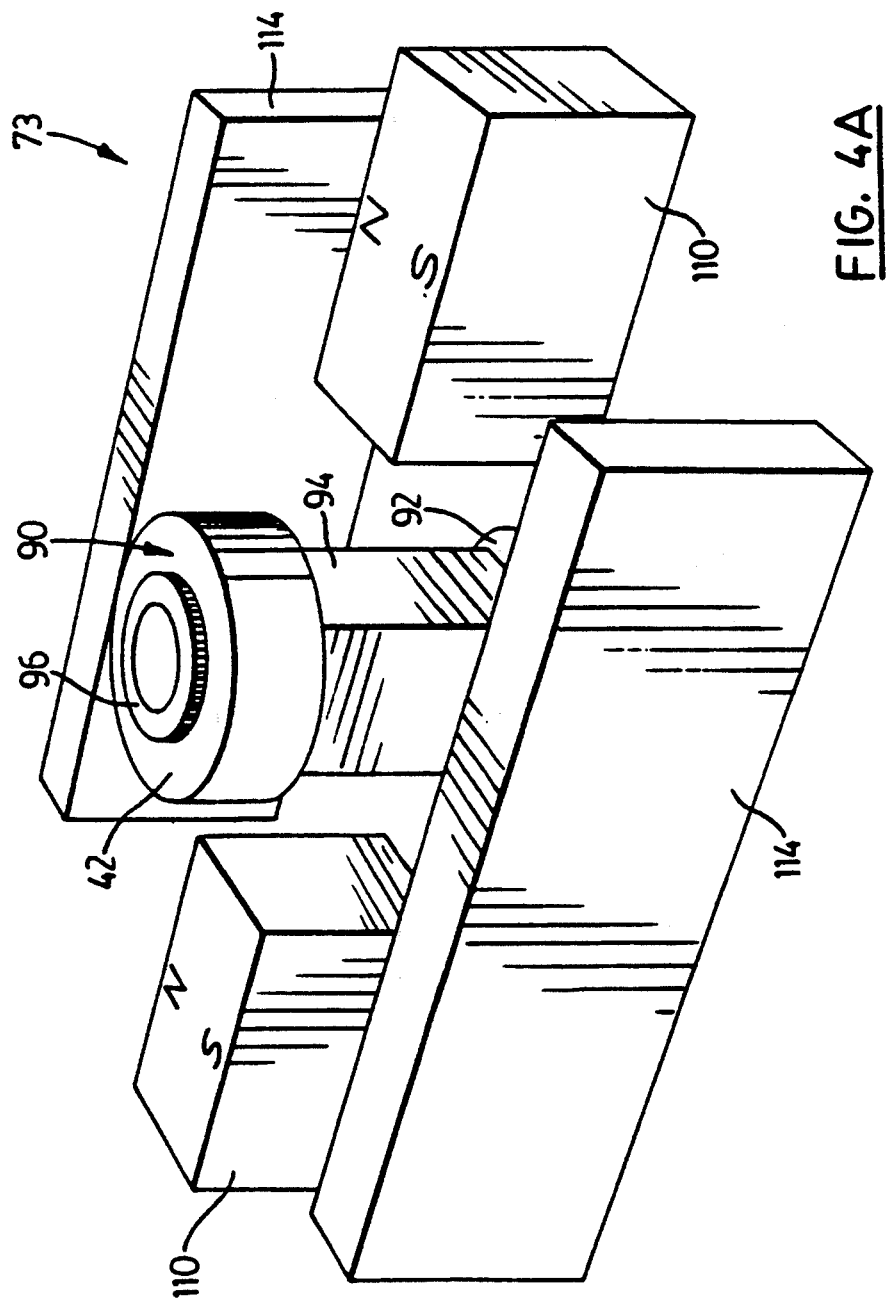
FIG. 4a is an exploded perspective view of an element forming part of the portion shown in FIGS. 2a and 2b.

The armature assembly 73 is oriented between the frame members 50,52 so that the coil assemblies 72 are located on opposite sides of its short dimension. As can been seen from FIGS. 4a to 4c, the armature assembly 73 includes an armature core 90 formed from stainless steel and having a pair of cylindrical portions 92 interconnected by a rectangular column 94. Annular bosses 96 of reduced diameter extend from the opposed outwardly facing sides of the cylindrical portions 92. The cylindrical portions 92 pass through a centrally located circular cut-out formed in the rectangular passage 98 provided in each frame member 52 which guide the movement of the armature assembly 73. The rectangular passages have inclined walls along their length so that the width of the passage at the inwardly facing sides of the frame members is more narrow than at the outwardly facing sides of the frame members. In particular, the width of each passage at the outwardly facing side of the frame members is equal to the diameter of the cut-outs while the width at the inwardly facing side of each frame member is less than the width of the armature assembly 73. This permits the frame members to act as stops to limit the movement of the armature assembly. A stainless steel screw 100 aligned with the cut-out 98a passes through an aperture in each spring 70 and through the rectangular passage in each frame member to engage threadably with internal threads provided in the armature core 90 so that movement of the armature assembly causes the bands to flex. Thus, the two bands 70b act against on another to bias the armature assembly 73 to a rest position equidistantly spaced from each frame member 50,52 respectively as the armature assembly moves.

Screw 100 passing upwardly through frame member 50 also acts to fasten the plunger member 46 to the outwardly facing side of the spring 70 so that the annular boss 46a formed thereon rests against the band 70b. A rubber O-ring 102 surrounds the plunger 46 to form a seal with the bottom section 38b of the transducer assembly casing 38.

A pair of magnets 110 formed from Samarium Cobalt are secured to opposed faces of the column 94 by cyanoacrylate and are dimensioned and arranged so that spaces 112 are provided between their upper and lower surfaces and the cylindrical portions 92. The magnets are also arranged so that the poles of each magnet are aligned and thus, face the same direction. Rectangular pole pieces 114 formed from cold rolled steel are secured to the other opposed faces of the column 94 and to the magnets 110 by cyanoacrylate and extend lengthwise slightly beyond the outer edge of the magnets. Thus, the pole pieces 114 serve to provide support for the armature assembly 73. The pole pieces are also dimensioned to provide a small gap 116 between their upper and lower surfaces and the cylindrical portions 92 and are spaced from the coils 76 to define gaps 114a. Since the magnets 110 are arranged with their poles aligned and since the pole pieces 114 extend the length of the magnets and are secured thereto, each pole piece 114 becomes a magnet with the same orientation as the smaller magnets 110. This allows the armature assembly 73 to function as a larger continuous magnet.

The leads 82 are electrically connected to the cable 32 via conductors (not shown) that are received in the jack 34 to allow the coils to be energized so that the armature vibrates the plunger 46. The frequency response of the transducer 28 ranges from between 50 Hz to 8,000 Hz making it suitable for use in both cutaneous nerve receptor communication and communication via bone conduction. The jack 34 is connected to the processing circuitry within the housing (best shown in FIGS. 6 and 7) which will now be described.

Figure 6:
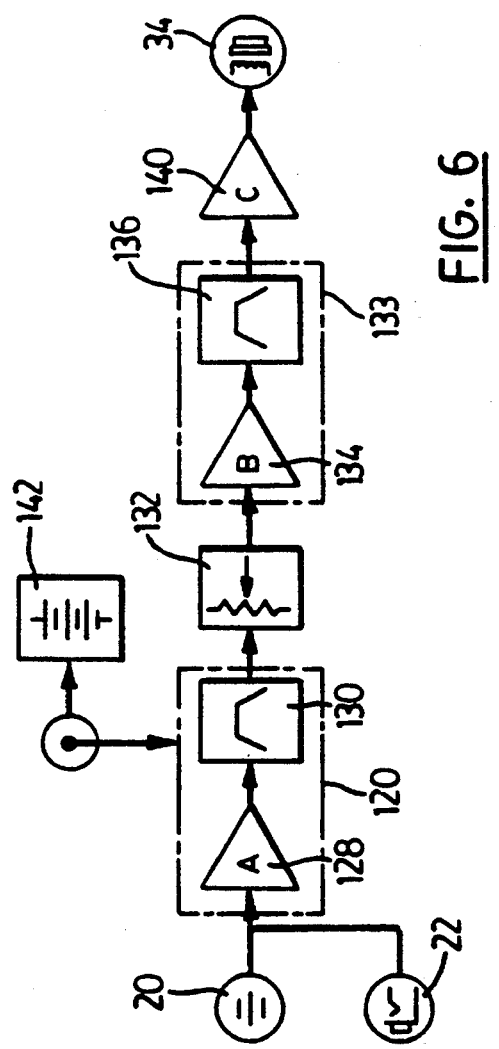
FIG. 6 is a block diagram illustrating another portion of the device shown in FIG. 1.

FIG. 6 shows the processing circuitry in simplified form. As can be seen, the processing circuitry includes the microphone 20 which is electrically connected to an active bandpass filter with gain 120. The external audio input signal jack 22 is also shown connected to the active bandpass filter with gain. The active bandpass filter 120 performs two functions, namely it operates as an audio frequency amplifier 128 and a bandpass filter 130 conveying its output to a potentiometer 132. The potentiometer 132 is controlled by the volume dial 18 so that the audio signal levels can be adjusted. The output of the potentiometer 132 is applied to a second active bandpass filter with gain 133. Similarly, the filter 133 functions as a second audio frequency amplifier 134 and a second bandpass filter 136. The output of the filter 133 is conveyed to a driver 140 which applies signals to the transducer assembly 14 via the jack 34 and cable 32. A battery 142 of the chargeable or non-chargeable type provides power to the components constituting the processing circuitry.

Figure 7:
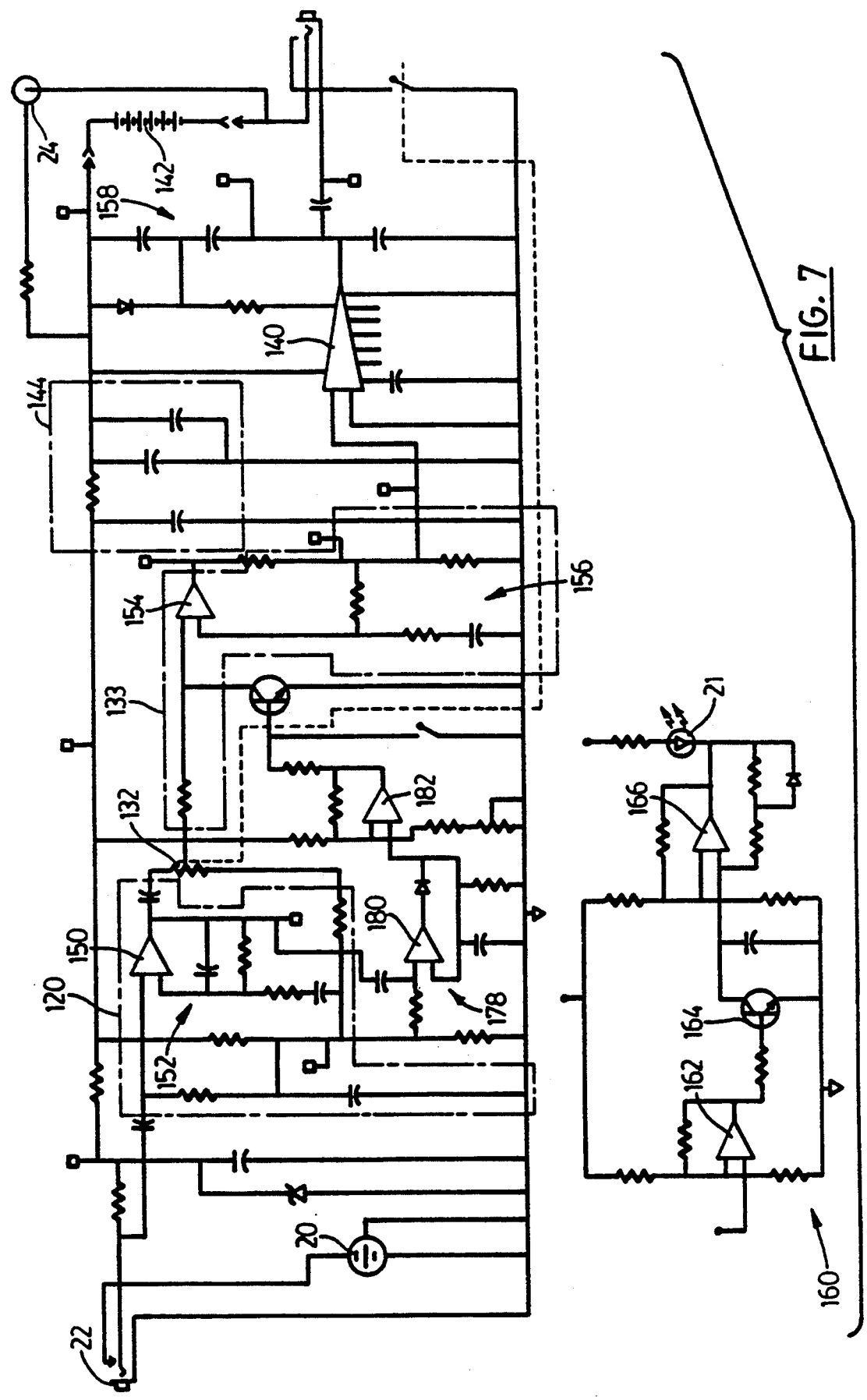
FIG. 7 is a wiring diagram of the portion shown in FIG. 6.

FIG. 7 better illustrates the processing circuitry. As can be seen, if a rechargeable battery 142 is used, it can be recharged via a jack 24 when a battery charger (not shown) is connected thereto. The jack 24 may also receive an alternative power supply should the battery 142 be missing or dead. A power supply filter 144 comprising a number of capacitors and a resistor receives the output voltage of the battery 142 before it is applied to the remainder of the processing circuitry.

As can be seen, the active bandpass filter 120 is comprised of an operational amplifier 150 and a resistor-capacitor arrangement 152. The output of the active bandpass filter 120 is conveyed to the potentiometer 132 which provides an output signal to the second active bandpass filter 133. The second active bandpass filter with gain is constituted by a second operational amplifier 154 and a second resistor-capacitor arrangement 156. The setting of the potentiometer 132 controls a switch SW2 connected to the output jack 34. This allows the device 10 to be shut off when the volume dial 18 is turned in the appropriate direction to its off position.

The second active filter 133 provides output signals to the voltage to current driver 140. The driver 140 which receives biasing from the battery 142 via an RC filter 158 provides the current output to the jack 34 which is then conveyed to the transducer assembly 14 via the cable 32.

Preferably, the frequency response of the circuitry is the same as the transducer 28 to allow the circuitry to operate the transducer to its potential. However, when using the device 10 for cutaneous nerve receptor communication, the frequency response of the circuitry is bandlimited to 3,000 Hz since this frequency represents the upper limit at which the cutaneous nerve receptors can detect audio information.

Power supply level monitoring circuitry 160 is also provided and includes a differential amplifier 162 receiving the filtered voltage VFILT from the battery 142. The differential amplifier 162 also receives a reference voltage VREF, the reference voltage being a scaled and regulated form of the filtered voltage. The differential amplifier 162 provides an output signal to the base of a transistor 164. The emitter of the transistor 164 is connected to ground GND while its collector thereof is connected to one terminal of a second differential amplifier 166. The other terminal of the differential amplifier 166 receives the filtered voltage. The output of the differential amplifier 166 is conveyed to one terminal of an LED 168 while the other terminal of the LED 168 receives the unfiltered voltage VBAT from the battery 142.

An audio signal mute circuit 178 is also provided and includes an operational amplifier 180 having one terminal connected to the GND via a capacitor C8 and a resistor R10 connected in parallel. The one terminal is also connected to one terminal of a second operational amplifier 182. The other terminal of amplifier 180 is connected to the filtered voltage VFILT via resistors R4 and R9 and receives the audio input signal from the microphone 20 or jack 22 via capacitor C7 from amplifier 150.

The output terminal of amplifier 180 is connected to the one terminal of amplifier 182 via a diode D1. The other terminal of the amplifier 182 is connected to the filtered voltage VFILT via a voltage divider comprising resistors R12, R15, and RV2. The output terminal of amplifier 182 is connected to the base of a transistor Q1. The collector of the transistor Q1 is connected to the output of the potentiometer 132 via a capacitor C9 while its emitter is connected to the ground. A switch S1 extends between the base of transistor Q1 and the ground GND. The mute circuit 178 is operable to inhibit the driver 140 from outputting driving signals if the input audio signals received by the microphone 20 are below a preset threshold as will be described herein.

The operation of the device 10 will now be described with reference to the FIGS. 1 to 7.

When using the present 10 for cutaneous nerve receptor communication, the band 30 is fastened around the wrist of the user so that the transducer assembly 14 is positioned with the bottom section 38b of the casing 38 against user's wrist. The housing 12 is conveniently located by the user in a pocket or is connected to a belt similar to a beeper system so that the microphone 20 is capable of receiving audio input signals. The cable 32 is inserted in the jack 34 to connect electrically the transducer 14 and the processing section 12. When input signals are received by the microphone 20 they are applied to the first active bandpass filter 120 which increases the signal level to a suitable audio level and performs the desired filtering. The output signals of the filter are then conveyed to the potentiometer 132. The potentiometer 132 which is adjustable via the volume dial 18 scales the filtered output of the active filter 120 to the appropriate level.

When the switch SW1 is opened, the auto mute circuit 178 is operational. When in this state, the operational amplifier 180 functions as a peak signal detector having a large discharge time. Depending on the magnitude of the input audio signal, the discharge time can be as long as five seconds. The second amplifier 182 functions as a level comparator and controls the operation of transistor Q1. Normally, transistor Q1 is biased to an "on" condition so that audio signals conveyed to the second active filter 133 from the potentiometer 32 that are below the threshold level as determined by the comparator 112 bypass the second active filter 133 and are instead conveyed to ground GND via the transistor Q1. This prevents signals from reaching the driver 140 and maintains the output of the processing circuitry nominally at zero.

When an input audio signal is received via the microphone 20 that has a peak greater than the threshold level set for the level comparator 182, the transistor Q1 bias is removed shutting off the transistor Q1 thereby allowing the audio signal to pass to the second active filter 133. The second active filter 133 adjusts and filters the received signal and applies it to the driver 140. The long discharge time of the amplifier 180 maintains the transistor Q1 in an "off" condition for a prolonged time to ensure that the entire signal is passed from the potentiometer 132 to the active filter 133.

Thus, when the microphone 20 is receiving no audio information of interest, the driver 140 receives little or no driving signals from the filter 133. This prevents background noise from causing the driver to actuate the transducer assembly in response to the noise and thereby conserves battery power. When useful audio information having a peak above the preset threshold level is received by the microphone 20, it is allowed to pass to the driver 140. When switch SW1 is moved to a closed condition, the transistor Q1 is continuously maintained in an off condition and thus, all audio information received by the microphone is conveyed to the driver 140 via the active filters 120, 133 and potentiometer 132.

As mentioned previously, the driver 140 converts the voltage applied to it from the active filter 133 into current signals which are supplied to the jack 34. The signals received by the jack 34 are conveyed to the transducer assembly 14 via the cable 32. Once the signals are received by the transducer assembly, they are applied to the coils 76 via the leads 82 thereby energizing the coils. Once the coils 76 are energized, an electromagnetic force is generated by each coil which cause the armature assembly 73 to move so that the armature assembly moves toward the frame member 50. As this occurs, the cylindrical portion 90 moves into the passage 98 via the cut-out 98a so that the annular boss 96 pushes the band 70b formed on the spring 70 secured to frame member 50 and pulls the band 70b formed on the other spring 70 into the passage 98 provided through frame member 52. This causes the plunger 46 to pass outwardly through the aperture 40 formed through the casing wall 38b and contact the user's skin. During movement of the plunger 46, the o-ring 102 provides a barrier to inhibit moisture and other contaminants from entering the transducer casing 38.

Since the driver 140 provides output signals to the transducer assembly 14 that are analogous to the audio information received by the microphone 20, the plunger 46 is vibrated by the armature assembly 73 in a manner analogous to the audio input signals. This of course provides vibrations to the cutaneous nerve receptors in the wrist so that the brain may interpret them without using the inner ear. When the output of the driver 140 drops low or if the device 10 is shut off via switch SW2, the springs 70 act to return the armature assembly 73 to its rest position suspended equidistantly from each frame member 50,52.

In addition, when the device 10 is turned on, the amplifier 162 compares the battery voltage with the reference voltage VREF set by an integrated circuit U4 which functions in a similar manner to a zener diode. If the scaled voltage is greater than the reference voltage, the amplifier 162 outputs a logic high voltage which in turn biases transistor 164 to an "on" condition. When transistor 164 is on, the voltage at the inverting terminal of amplifier 166 is lower than the voltage on its non-inverting terminal. This maintains the output of the amplifier 166 substantially high to prevent the LED 21 indicator lamp from being turned on.

When the scaled voltage falls below the reference voltage, the transistor 164 is turned off. This allows the amplifier 166 and its associated components to oscillate with a frequency of approximately $\frac{1}{2}$ Hz. Thus, the LED 21 becomes illuminated approximately 10% of the time during the oscillation thereby causing the LED 21 to flicker indicating a low battery condition.

It should be apparent that with the use of the jack 22, the microphone 20 can be by-passed to allow audio information from another source to be used to actuate the transducer assembly 14 such as an alternative microphone 23, a tape recorder, radio transceiver or the like. Since the assembly as shown is designed to be worn around the wrist of a user so that audio information is transmitted to the cutaneous nerve receptors of the user, the device 10 is particularly useful in the medical environment to assist the hearing impaired. It is also useful in the communications industry in a "Bell-Boy" type application to allow information to be transmitted to the user even though the user may be engaged in other verbal communication.

Although shown as being mounted on a wrist watch band, the transducer 28 may also be mounted on other apparel to be worn by a user to allow audio communication to occur without transmitting the information through the air to the user's ear structure. For example, in the industrial environment where noise often tends to be excessive and where ear muffs are often worn, verbal communication is difficult and often impossible. However, with the present transducer 28 communication between parties in this environment is possible by making use of the ear structure's ability to decipher vibrations conveyed thereto by bone conduction. Thus, in these types of environments, the transducer 28 is mounted in a safety helmet in a manner such that the plunger member 46 contacts the user's skin above the neck in a vibrational pattern analogous to the audio information being transmitted to the user. The vibrations are then conveyed to the user's ear structure via bone conduction allowing the audio information to be deciphered. Thus, audio communication is facilitated even in the noisiest environments.

In addition, the present transducer can be used in the telecommunications industry. For example, the transducer can be used in conjunction with or to replace the receiver of a telephone handset. In this case, the transducer assembly is connected to the audio lines typically connected to the receiver in the telephone handset and mounted in a headset so that the plunger member contacts the user's head in response to audio signals received over the telephone network thereby allowing the user's ear structure to receive the audio information via bone conduction. Alternatively, the wrist watch band mounted transducer can be used and connected to the receiver audio lines to permit reception of the audio signals via the user's cutaneous nerves.

In environments such as surveillance, the transducer 28 can be mounted on the frame work of a pair of Glasses making the wearer less conspicuous while still allowing audio information to be conveyed to the user's ear structure via bone conduction.

To determine the performance of the present invention, a number of prelingually deaf subjects (seven adults and five children) were tested with and without the present device 10. The device 10 as used in the tests was in the form shown in the Figures so that audio information was conveyed to the cutaneous nerve receptors at the subject's wrists. The subjects were all male with the exception of one female child with the average age of the adult subjects being 31.9 years and the child subjects being 11.6 years.

To begin each subject was given a hearing test using a Madsen OB 822 audiometer with TDH 49 earphones for the threshold procedure. Thresholds were obtained at octave intervals from 250 Hz to 4,000 Hz. All testing was done in a doubled wall Tracoustics 254 sound suite.

Once the thresholds were obtained, a series of sound detection tests were performed in a free field condition with the subject seated at 0° azimuth one meter in front of a load speaker. The stimuli used for all sound detection tests were generated by the audiometer and all instruments were calibrated to ANSI standards. The sound detection tests were performed in an unaided and then an aided condition if the subject wore a hearing aid. The tests were then performed on the subjects with the subjects wearing the present communication device.

The first sound test was an evaluation of the subject's perception of warble tones. The warble tones presented were at a 4% frequency modulation rate and the testing was done at octave intervals from 250 Hz to 4,000 Hz. Sound detection to a broadband noise shaped to mask speech was then measured and lastly detection to the lowest level of speech was evaluated. The speech stimulus used was a CID recording of Spondee words (W-1).

A speech reading evaluation was then performed utilizing the Utley Sentence Test (1946). A female speaker presented the sentences seated one meter from the subjects at an average presentation level of 48.5 dB SPL as measured by a Quest model 1800 sound level meter. The speech reading protocol was as follows:
1. A nonvisual unaided presentation was given;
2. A visual unaided presentation was given;
3. A visual presentation was given while the subject was wearing their own hearing aid; and
4. The visual presentation was given while the subject was wearing the present communication device.

The results of the tests were as follows:

WARBLE TONES

As can be seen from Table I, the present communication device clearly improved perception of warble tones for both adults and children in the frequency range of 50 Hz to 1,000 Hz. Of particular interest was the improved sound detection of subjects wearing the present device at 1,000 Hz. This is in view of the fact that conventional single channel vibrotactile devices do not provide much stimulation above 500 Hz.

TABLE I

Mean improvement scores for sound detection of warble tones resulting from wearing the Bionic device

| Frequency (Hz.) | 250 | 500 | 1000 | 2000 | 4000 |
| --- | --- | --- | --- | --- | --- |
| Adults | 45.8 dB | 45.8 dB | 43 dB | — | — |
| Children | 47.5 dB | 42.2 dB | 47.5 dB | — | — |

Because the child subjects all had their own hearing aid, a comparison of sound detection with the children wearing their own hearing aid and the present device 10 was made. The results of this comparison are shown in Table II and as should be noted the present device clearly improved sound detection in the lower frequency ranges over conventional hearing aids.

TABLE II

Mean improvement scores for sound detection of warble tones.

| Frequency | 250 Hz. | 500 Hz. | 1000 Hz. |
| --- | --- | --- | --- |
| Conventional Aid | 6.2 dB | 23.2 dB | 46.6 dB |
| Bionic Device | 47.5 dB | 42.2 dB | 47.5 dB |
| Difference | 41.3 dB | 19 dB | 0.9 dB |

SPEECH NOISE AND SPEECH

The findings for both speech and speech shaped noise were similar and the results of these tests are shown in Table III. As can be seen from the results, when the subjects were wearing the present device 10, they were able to detect the presence of speech and speech noise at a level 42.5 dB to 48.3 dB lower (or better) than when they were not wearing the present device 10. The same test were performed with the child subjects while they wore their conventional hearing aid. The results of this test showed that the present device 10 provided between 18 dB to 25 dB better sound detection than the conventional hearing aids.

TABLE III

Mean improvement scores for sound detection of speech and speech noise resulting from wearing the Bionic device

| | Speech | Speech Noise |
| --- | --- | --- |
| Adults | 48.3 dB | 43.3 dB |
| Children | 42.5 dB | 42.5 dB |

SPEECH READING

The results of this test were very different between the adult and child subjects. The adults showed no significant increase in speech reading test scores from the unaided condition to the aided condition with the present device 10. This finding was not unusual and had been reported in earlier research (Blamey et al 1985).

In contrast, the child subjects demonstrated a significant improvement in speech reading scores from the unaided condition to the aided condition with the present device (40% improvement) but also even a greater improvement in the aided condition with their own conventional hearing aid (50% improvement).

In conclusion it was found that the present device improved sound detection significantly in the low frequencies up to and including 1,000 Hz. It was also found that the present device 10 improved both speech and speech noise even to a greater extent than conventional hearing aids.

I claim:
1. A communication device for transmitting audio information to a user comprising:

input means for receiving input audio signals;

processing means in communication with said input means and converting said input audio signals into transducer driving signals;

a transducer assembly to be worn by a user and being in communication with said processing means, said transducer assembly including a plunger member moveable axially to contact said user; drive means including an armature to which said plunger member is attached, said drive means moving said armature axially to cause said plunger member to contact said user in a vibrational pattern analogous to said input audio signals in response to said transducer driving signals; and biasing means at opposite axial ends of said armature for opposing the movement of said armature in response to said transducer driving signals and for returning said armature to a datum in the absence of said transducer driving signals.

2. A device as defined in claim 1 wherein each said biasing means is in the form of a spring attached to said armature.

3. A device as defined in claim 2 wherein said drive means further includes a pair of coils each surrounding a core and being located on opposite sides of said armature, said coils generating an electromagnetic force when energized by said transducer driving signals and causing said armature to move said plunger member.

4. A device as defined in claim 3 wherein said springs are formed from beryllium-copper.

5. A device as defined in claim 3 wherein said armature includes a generally rectangular armature core having first and second pairs of opposed faces; a pair of magnets with each magnet extending outwardly from one face of said first pair of opposed faces along a first axis, said magnets also being arranged so that their magnetic poles face the same direction; and a pair of pole pieces with each pole piece being secured to one face of said second pair of opposed faces, said pole pieces extending lengthwise parallel to said first axis, each of said pole pieces also being secured to both of said magnets.

6. A device as defined in claim 5 wherein said pole pieces extend lengthwise beyond the outer edges of said magnets.

7. A device as defined in claim 6 wherein said transducer assembly further comprises a pair of axially spaced frame members, said armature and said coils being located therebetween, said armature being positioned by said springs to said datum whereby said armature is positioned equidistantly from each of said frame members, said frame members constituting stops to limit the range of movement of said armature when driven by said electromagnetic forces.

8. A device as defined in claim 1 wherein said input means is in the form of a miniaturized microphone and said processing means includes audio amplifying means and filtering means for converting said input audio signals into said transducer driving signals, said amplifying and filtering means being disposed within a compact housing.

9. A device as defined in claim 8 wherein said amplifying and filtering means is constituted by a pair of active bandpass filters having signal gain capabilities.

10. A device as defined in claim 9 wherein said transducer assembly is mounted on a band adapted to be secured to the wrist of a user and is removeably connected to said processing means.

11. A device as defined in claim 9 wherein said processing means further includes a removable power supply located within said housing.

12. A device as defined in claim 11 wherein said power supply is rechargeable and wherein said processing means includes means provided through said housing for permitting a recharging device to recharge said power supply.

13. A device as defined in claim 12 wherein said processing means further includes second audio input means for permitting an alternate audio signal source to provide said audio input signals, said microphone being conditioned to an inoperative state when said second audio input means is in use.

14. A device as defined in claim 1 wherein said transducer assembly is located in a safety helmet.

15. A device as defined in claim 1 wherein said transducer assembly is located in the framework of a pair of glasses.

16. A transducer assembly for use in a communication device for transmitting audio information to a user comprising:

a casing;

a plunger member within said casing and being moveable axially through an aperture in said casing to contact said user;

drive means within said casing and including an armature to which said plunger member is attached, said drive means moving said armature axially to cause plunger member to contact said user in a vibrational pattern in response to driving signals analogous to audio information to be transmitted to said user; and biasing means at opposite axial ends of said armature for opposing movement of said armature in response to said driving signals and for returning said armature to a datum in the absence of said driving signals.

17. An assembly as defined in claim 16 wherein each said biasing means is in the form of a spring attached to said armature.

18. An assembly as defined in claim 17 wherein said drive means further comprises a pair of coils with each coil surrounding a core, said cores being located on opposite sides of said armature, said coils generating an electromagnetic force when energized by said driving signals and causing said armature to move said plunger member.

19. An assembly as defined in claim 18 wherein said armature includes a generally rectangular armature core having first and second pairs of opposed faces; a pair of magnets with each magnet extending outwardly from one face of said first pair of opposed faces along a first axis, said magnets also being arranged so that their magnetic poles face the same direction; and a pair of pole pieces with each pole piece being secured to one face of said second pair of opposed faces, said pole pieces extending lengthwise parallel to said first axis, each of said pole pieces also being secured to both of said magnets.

20. An assembly as defined in claim 19 wherein said pole pieces extend lengthwise beyond the outer edges of said magnets.

21. An assembly as defined in claim 20 further comprising a pair of frame members spaced apart along an axis with said coils and armature being located between said frame members, said springs being secured to said frame members, said frame members being provided with passages to permit said armature to enter said passages, deflect said springs and move said plunger member, said springs maintaining said armature at said datum equidistantly spaced from said frame members in the absence of said driving signals, said frame members constituting stops to limit the range of movement of said armature when driven by said electromagnetic forces.

22. An assembly as defined in claim 21 wherein each of said springs includes a pair of parallel slots formed therein to define a band having increased flexibility, said band being attached to said armature and deflecting upon movement of said armature.

23. An assembly as defined in claim 16 wherein said plunger member is moved axially by said armature at a frequency of from between 50 Hz to 8,000 Hz in response to said driving signals.

24. The assembly as defined in claim 16 wherein said plunger member is moved axially by said armature at a frequency of from between 50 Hz to 3,000 Hz in response to said driving signals.

25. A communication device for transmitting audio information to a user comprising:
a compact housing adapted to facilitate carrying by a user;
a miniaturized microphone in said housing for receiving input audio signals;
processing means in said housing and being in communication with said microphone, said processing means converting said input audio signals into transducer driving signals;
a transducer assembly to be worn by said user and being in communication with said processing means, said transducer assembly including a plunger member moveable axially to contact said user; drive means including an armature to which said plunger member is attached, said drive means moving said armature axially to cause said plunger member to contact said user in a vibrational pattern analogous to said input audio signals in response to said transducer driving signals; and biasing means at opposite axial ends of said armature for opposing the movement of said armature in response to said transducer driving signals and for returning said armature to a datum in the absence of said transducer driving signals.

26. A device as defined in claim 25 wherein said processing means includes audio amplifying means and filtering means for converting said input audio signals into said transducer driving signals.

27. A device as defined in claim 26 wherein said amplifying and filtering means is constituted by a pair of active bandpass filters with signal gain capabilities.

28. A device as defined in claim 27 wherein said processing means further includes a removable power supply located within said housing.

29. A device as defined in claim 28 wherein said power supply is rechargeable and wherein said processing means includes means provided through said housing for permitting a recharging device to recharge said power supply.

30. A device as defined in claim 29 wherein said processing means further includes second audio input means for permitting an alternate audio signal source to provide said audio input signals, said microphone being conditioned to an inoperative state when said second audio input means is in use.

31. A device as defined in claim 30 wherein said transducer assembly is mounted on a band adapted to be secured to the wrist of a user and is removeably connected to said processing means.

32. A device as defined in claim 25 wherein said processing means further comprises input signal mute means for inhibiting generation of said transducer driving signals by said processing means when said input audio signals are below a predetermined threshold.

33. A device as defined in claim 25 wherein said transducer assembly is mounted in a helmet.

34. A device as defined in claim 25 wherein said transducer assembly is mounted in the framework of a pair of glasses.

35. A transducer assembly for use in a communication device for transmitting audio information to a user comprising:
a casing;
a plunger member within said casing and being moveable axially through an aperture in said casing to contact said user;
drive means within said casing and including an armature to which said plunger member is attached and a pair of coils with each coil surrounding a core, said coils being located on opposite sides of said armature, said coils generating an electromagnetic force when energized by said driving signals to move said armature axially to cause plunger member to contact said user in a vibrational pattern in response to driving signals analogous to audio information to be transmitted to said user, said armature including a generally rectangular armature core having first and second pairs of opposed faces; a pair of magnets with each magnet extending outwardly from one face of said first pair of opposed faces along a first axis, said magnets also being arranged so that their magnetic poles face the same direction; and a pair of pole pieces with each pole piece being secured to one face of said second pair of opposed faces, said pole pieces extending lengthwise parallel to said first axis and beyond the outer edges of said magnets, each of said pole pieces also being secured to both of said magnets;
biasing means in the form of a pair of springs each attached to an opposite end of said armature for opposing movement of said armature in response to said driving signals and for returning said armature to a datum in the absence of said driving signals, each of said springs including a pair of parallel slots formed therein to define a band having increased flexibility, said band being attached to said armature and deflecting upon movement of said armature; and
a pair of frame members spaced apart along an axis with said coils and armature being located between said frame members, said springs also being secured to said frame members, said frame members being provided with passages to permit said armature to enter said passages, deflect said springs and move said plunger member, said frame members constituting stops to limit the range of movement of said armature when driven by said electromagnetic forces.

36. A transducer assembly for use in a communication device for transmitting audio information to a user comprising:
a casing;
a plunger member within said casing and being moveable axially through an aperture in said casing to contact said user;

an armature within said casing and being attached to said plunger member, said armature being moveable axially to move said plunger member to contact said user;

drive means including a pair of coils with each coil surrounding a core and being located on opposite sides of said armature, said coils generating an electromagnetic force when energized by said driving signals to move said armature, said armature moving said plunger member so that said plunger member contacts said user in a vibrational pattern analogous to said audio information;

biasing means in the form of a pair of springs each attached to an opposite end of said armature for opposing movement of said armature in response to said driving signals and for returning said armature to a datum in the absence of said driving signals, each of said springs including a pair of parallel slots formed therein to define a band having increased flexibility, said band being attached to said armature and deflecting upon movement of said armature; and a pair of frame members spaced apart along an axis with said coils and armature being located between said frame members, said springs also being secured to said frame members, said frame members being provided with passages to permit said armature to enter said passages, deflect said springs and move said plunger member, said frame members constituting stops to limit the range of movement of said armature when driven by said electromagnetic forces.

37. A communication device for transmitting audio information to a user comprising:

input means for receiving input audio signals;

processing means in communication with said input means and converting said input audio signals into transducer driving signals;

a transducer assembly to be worn by a user and being in communication with said processing means, said transducer assembly including a plunger member moveable axially to contact said user; drive means including an armature to which said plunger member is attached, said drive means moving said armature axially to cause said plunger member to contact said user in a vibrational pattern analogous to said input audio signals in response to said transducer driving signals; and biasing means at opposite ends of said armature for opposing the movement of said armature in response to said transducer driving signals and for returning said armature to a datum in the absence of said transducer driving signals, said biasing means being in the form of a pair of springs each attached to an opposite end of said armature, each of said springs including a pair of parallel slots formed therein to define a band having increased flexibility, said band being attached to said armature and deflecting upon movement of said armature.

38. A communication device as defined in claim 37 further comprising a pair of frame members spaced apart along an axis with said drive means and armature being located between said frame members, said springs also being secured to said frame members, said frame members being provided with passages to permit said armature to enter said passages, deflect said springs and move said plunger member, said frame members constituting stops to limit the range of movement of said armature.

39. A transducer assembly for use in a communication device for transmitting audio information to a user comprising:

a casing;

a plunger member within said casing and being moveable axially through an aperture in said casing to contact said user;

drive means within said casing and including an armature to which said plunger member is attached, said drive means moving said armature axially to cause plunger member to contact said user in a vibrational pattern in response to driving signals analogous to audio information to be transmitted to said user; and biasing means at opposite ends of said armature for opposing the movement of said armature in response to said transducer driving signals and for returning said armature to a datum in the absence of said transducer driving signals, said biasing means being in the form of a pair of springs each attached to an opposite end of said armature, each of said springs including a pair of parallel slots formed therein to define a band having increased flexibility, said band being attached to said armature and deflecting upon movement of said armature.

40. A transducer assembly as defined in claim 39 further comprising a pair of frame members spaced apart along an axis with said drive means and armature being located between said frame members, said springs also being secured to said frame members, said frame members being provided with passages to permit said armature to enter said passages, deflect said springs and move said plunger member, said frame members constituting stops to limit the range of movement of said armature.

41. A transducer assembly as defined in claim 39 wherein said drive means is in the form of a pair of coils surrounding a core and being located on opposite sides of said armature, said coils generating an electromagnetic force when energized by said driving signals to move said armature.

* * * * *